United States Patent [19]

Schreiber

[11] 4,016,039

[45] Apr. 5, 1977

[54] PROCESS FOR THE RECOVERY OF PROTEINS FROM AQUEOUS SOLUTIONS OF PROTEINS

[75] Inventor: Wolfgang Schreiber, Langenfield, Germany

[73] Assignee: Henkel & Cie G.m.b.H., Dusseldorf-Holthausen, Germany

[22] Filed: Mar. 22, 1976

[21] Appl. No.: 668,840

[30] Foreign Application Priority Data

Mar. 22, 1975 Germany .......................... 2512735

[52] U.S. Cl. ........................... 195/66 R; 260/112 R
[51] Int. Cl.² ........................................ C07G 7/028
[58] Field of Search ............. 195/66 R, 66 A, 66 B; 260/112 R

[56] References Cited

UNITED STATES PATENTS 3,513,074   5/1970   Matsuoka et al. ............... 195/66 R

*Primary Examiner*—Lionel M. Shapiro
*Attorney, Agent, or Firm*—Hammond & Littell

[57] ABSTRACT

An improved process for the recovery of proteins from aqueous solutions of proteins, for example, proteases from fermenter solutions, by precipitation by means of salts and filtration, optionally with the use of common filtration aids, which is characterized in that a polyoxyethylene glycol having a molecular weight of 400 to 1,000, preferably 500 to 800, is added in an amount of from 0.5 to 3% by weight to the aqueous solution of proteins before said precipitation.

11 Claims, No Drawings

PROCESS FOR THE RECOVERY OF PROTEINS FROM AQUEOUS SOLUTIONS OF PROTEINS

RELATED ART

The recovery of proteins from aqueous solutions of proteins, for example, proteases from fermenter solutions, is usually effected by precipitation by means of additions thereto of salt (salting out) and subsequent filtration. The precipitation is effected at room temperature or at a slightly elevated temperature up to about 50° C using, as a rule, inorganic salts, such as NaCl, $CaCl_2$ $MgCl_2$, $MgSO_4$ and preferably $Na_2SO_4$. Usually the aqueous solutions of proteins are concentrated before precipitation to a minimum protein content of about 2%. In order to shorten the filtration times, which are as a rule very long and, in addition, fluctuate greatly from charge to charge, common filtration aids can be added before filtration, such as starch, kieselguhr, cellulose powder, bleaching clays, colloidal silica, precipitated sodium aluminosilicates, etc. These filtration aids, however, cannot always solve the problem satisfactorily and frequently result in an undesired impurity in the protein recovered.

OBJECTS OF THE INVENTION

An object of the present invention is the development, in the process for recovering proteins from aqueous solutions of proteins comprising the steps of adding a sufficient amount of a water-soluble inorganic salt to an aqueous solution of proteins to effect precipitation of said proteins, filtering the aqueous solution containing the precipitated protein in the presence of from 0 to 4% by weight of filter aids, and recovering said precipitated protein, of the improvement which consists in adding from 0.5 to 3% by weight of a polyoxyethylene glycol having an average molecular weight of from 400 to 1,000 to said aqueous solution of proteins before adding said inorganic salts.

This and other objects of the present invention will become more apparent as the description thereof proceeds.

DESCRIPTION OF THE INVENTION

The subject of the present invention is an improvement in the process for recovering proteins from aqueous solutions of protein, for example, proteases from fermenter solutions, by precipitation by means of salts and filtration, if necessary, using in addition common filtering aids, characterized in that a polyoxyethylene glycol with an average molecular weight of 400 to 1,000, preferably 500 to 800, is added to the protein solution before the precipitation in an amount of 0.5 to 3% by weight, preferably from 1 to 2% by weight. The percent by weight is based on the entire aqueous solution of proteins.

More particularly, the present invention relates, in the process for recovering proteins from aqueous solutions of proteins comprising the steps of adding a sufficient amount of a water-soluble inorganic salt to an aqueous solution of proteins to effect precipitation of said proteins, filtering the aqueous solution containing the precipitated protein, in the presence of from 0 to 4% by weight of filter aids, and recovering said precipitated protein, to the improvement which consists in adding from 0.5 to 3% by weight of a polyoxyethylene glycol having an average molecular weight of from 400 to 1,000 to said aqueous solution of proteins before adding said inorganic salt.

The polyoxyethylene glycols utilized are known products. They are obtained by polymerization of ethylene oxide in the presence of catalysts, preferably under pressure. Particularly suitable is a polyoxyethylene glycol with an average molecular weight of 600. The preferred amount used is 1 to 2% by weight, based on the protein solution.

Due to the addition of polyoxyethylene glycol according to the invention, the filterability of the slurry of precipitated protein in the aqueous salt solution is decisively improved, that is, the required filtering times are substantially reduced under otherwise identical conditions. The improvement is also achieved when common filtering aids, as they are mentioned above, are also used.

It was found, surprisingly, that the effect of the polyoxyethylene glycols is quite specific and is limited to the claimed relatively narrow average molecular weight range of 400 to 1,000, preferably 500 to 800. The optimum is at the average molecular weight of 600. This behavior probably has something to do with the possible precipitation of the polyoxyethylene glycols of various molecular weights by the salts used in the precipitation. However, applicants are not certain as to the reasons for this and a final clarification of these questions is still outstanding.

A further improvement in filterability can be achieved by adding to the protein solution during the precipitation, together with the polyoxyethylene glycol, a water-soluble polymer which is precipitated at lower salt concentrations than the protein present. Suitable polymers are polyvinyl alcohol and polyvinyl pyrrolidone. The amounts required are about 0.5 to 2% by weight, preferably 1% by weight, based on the aqueous solution of proteins. These polymers by themselves do not facilitate the filtration, but they can be used in combination with the polyoxyethylene glycols according to the invention and act then in a similar manner as the known water-insoluble filtrating aids by imparting to the filter cake a drier and firmer consistency and by facilitating its detachment from the filter.

Among the conventional filter aids employed, the optimum appears to be kieselguhr or a precipitated sodium aluminosilicate, such as those described in the copending commonly assigned U.S. patent application Ser. No. 458,306, filed Apr. 5, 1974. The water-insoluble filter aids are employed in amounts of from 0.5 to 2% by weight, based on the weight of the protein solution.

The inorganic salts utilized in the precipitation are those discussed above. They are added to the aqueous solutions of proteins containing the polyoxyethylene glycol in an amount sufficient to cause precipitation of the protein. This will vary depending on the type of salt employed and the amount of protein present, as well as the pH and temperature of the aqueous solution. Preferably amounts of from 5 to 50% by weight, based on the protein solution are employed at a pH range of from 4 to 7.5.

The process according to the invention is used primarily for the recovery of enzymes, particularly proteases, such as alkaline proteases, from fermenter solutions, and the like.

The following examples are illustrative of the invention without being limitative in any respect.

EXAMPLE 1

A fermenter broth of *bacillus licheniformis*, which contains an alkaline protease and which was prepared according to the process described in German published patent application DOS No. 2,063,988, was liberated of cell residues and concentrated, as described likewise in the Example 3 of the DOS. 2% by weight of polyoxyethylene glycols of different average molecular weights were added to this concentrate. The subsequent precipitation of the protease was effected by the addition of 25% by weight of anhydrous sodium sulfate at a pH of 5. The filtration was effected with a Buchner funnel under the same controlled conditions. Table 1 shows the filtration times determined for 1 liter of concentrate.

TABLE 1

Filtration Times with Polyoxyethylene Glycols of Different Average Molecular Weights

| Average Molecular Weight | Filtration Time (in % of the same Batch Without Any Addition) |
|---|---|
| 300 | 138 |
| 400 | 53 |
| 600 | 4 |
| 1,000 | 91 |
| 4,000 | 100 |
| 12,000 | 127 |

The test values show that a marked improvement of the filtration times can only be achieved with polyoxyethylene glycols of an average molecular weight of 400 to 1,000. The optimum is at an average molecular weight of 600, where the filtration time is only 4% of the time required in the absence of additives.

EXAMPLE 2

Under the same conditions as indicated in Example 1, the amount of polyoxyethylene glycol 600 was varied in order to determine the optimum amount to be added. As it can be seen from the following Table 2, the filtration time decreased continually up to an addition of 2% by weight. No improvements were achieved by further increasing the amount added, while the isolated products had a slightly oily, relatively dark appearance after freeze-drying, which is probably due to a too high content of polyoxyethylene glycol 600.

TABLE 2

Filtration Time with Additions of Different Amounts of Polyoxyethylene Glycol 600

| Amount Added | Filtration Time for 100 ml |
|---|---|
| 0 | 18 min. 40 sec. |
| 0.6 | 11 min. 40 sec. |
| 1 | 11 min. 0 sec. |
| 1.5 | 2 min. 15 sec. |
| 2 | 2 min. 30 sec. |

EXAMPLE 3

The addition of water-insoluble filtering aids which are used to improve the filter cake, does not impair the improved filterability effect of the addition of polyoxyethylene glycol 600. The same holds true for the additional use of water-soluble polymer, like polyvinyl alcohol which is precipitated at a lower salt concentration than the protein. The following Table III shows the filtration times with and without the addition of polyoxyethylene glycol 600 and in the presence of different filtering aids.

TABLE 3

Effect of Polyoxyethylene Glycol 600 In the Presence of Various Filtration Aids

| Charge (Fermenter Broth) | Addition of Polyglycol 600 | Filtration Aid | Filtration Time (in minutes) |
|---|---|---|---|
| 1 | — | — | 72.1 |
| | — | 1% corn starch | 43.8 |
| | 1.5% | 1% corn starch | 10.7 |
| 2 | — | — | 31.3 |
| | — | 1% Na aluminosilicate | 38.2 |
| | 1.5% | 1% Na aluminosilicate | 1.6 |
| 3 | — | — | 31.3 |
| | — | 1% polyvinyl alcohol | 44.5 |
| | 1.5% | 1% polyvinyl alcohol | 9.25 |
| 4 | — | — | 31.3 |
| | — | 1% kieselguhr | 26.8 |
| | 1.5% | 1% kieselguhr | 1.3 |
| | — | 1% cellulose powder | 30.2 |
| | 1.5% | 1% cellulose powder | 4.8 |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. In the process for recovering an alkaline protease from the fermentation of *Bacillus licheniformis* in aqueous solutions comprising the steps of adding a sufficient amount of a water-soluble inorganic salt to an aqueous solution of an alkaline protease from the fermentation of *Bacillus licheniformis* to effect precipitation of said alkaline protease, filtering the aqueous solution containing the precipitated alkaline protease in the presence of from 0 to 4% by weight of filter aids, and recovering said precipitated alkaline protease, the improvement which consists in adding from 0.5 to 3% by weight of a polyoxyethylene glycol having an average molecular weight of from 400 to 1,000 to said aqueous solution of alkaline protease before adding said inorganic salt.

2. The process of claim 1 wherein said polyoxyethylene glycol has an average molecular weight of from 500 to 800.

3. The process of claim 1 wherein said polyoxyethylene glycol has an average molecular weight of 600.

4. The process of claim 1 wherein said polyoxyethylene glycol is employed in an amount of from 1 to 2% by weight.

5. The process of claim 1 wherein a further addition of from 0.5 to 2% by weight of a water-soluble polymer which is precipitated at a lower salt concentration than said alkaline protease is made to said aqueous solution of alkaline protease before adding said inorganic salt.

6. The process of claim 5 wherein 1% by weight of said water-soluble polymer is added.

7. The process of claim 5 wherein said water-soluble polymer is selected from the group consisting of polyvinyl alcohol and polyvinyl pyrrolidone.

8. The process of claim 1 wherein said filter aids are employed in the amount of from 0.5 to 2% by weight.

9. The process of claim 8 wherein said filter aids are selected from the group consisting of starch, kieselguhr, cellulose powder, bleaching clay, colloidal silica and a precipitated sodium aluminosilicate.

10. The process of claim 8 wherein said filter aid is kieselguhr.

11. The process of claim 8 wherein said filter aid is a precipitated sodium aluminosilicate.

* * * * *